United States Patent [19]
Buttgen et al.

[11] Patent Number: 6,015,396
[45] Date of Patent: Jan. 18, 2000

[54] AUTOMATIC CANNULA WITHDRAWING DEVICE FOR INJECTION SYRINGES

[75] Inventors: Heinz Buttgen, Jona; Konrad Burger, Eschenbach; Tilo Callenbach; Karl Mazenauer, both of Jona; Daniel Riesen, Bubikon; Daniel Vuille, Buchelstrasse 5, Ch-8732 Neuhaus, all of Switzerland

[73] Assignees: H. Weidmann AG Weidmann, Rapperswil; Daniel Vuille, Neuhaus, both of Switzerland

[21] Appl. No.: 08/981,540
[22] PCT Filed: Jul. 2, 1996
[86] PCT No.: PCT/CH96/00243
  § 371 Date: Dec. 12, 1997
  § 102(e) Date: Dec. 12, 1997
[87] PCT Pub. No.: WO97/02060
  PCT Pub. Date: Jan. 23, 1997

[30] Foreign Application Priority Data

Jul. 6, 1995 [CH] Switzerland .......................... 1973/95

[51] Int. Cl.⁷ .................................................. A61M 5/32
[52] U.S. Cl. ........................ 604/192; 604/110; 604/198; 604/136; 604/137
[58] Field of Search ...................... 604/110, 272, 604/198, 136, 137, 138, 162, 164, 165

[56] References Cited

U.S. PATENT DOCUMENTS

| | | |
|---|---|---|
| 4,747,831 | 5/1988 | Kulli ........................................ 604/110 |
| 5,114,404 | 5/1992 | Paxton et al. . |
| 5,180,369 | 1/1993 | Dysarz . |

FOREIGN PATENT DOCUMENTS

| | | |
|---|---|---|
| 290176 | 11/1988 | European Pat. Off. . |
| 566882 | 10/1993 | European Pat. Off. . |
| 9205818 | 4/1992 | WIPO . |
| 9216248 | 10/1992 | WIPO . |

*Primary Examiner*—Corrine McDermott
*Assistant Examiner*—Kent Gring
*Attorney, Agent, or Firm*—Sughrue, Mion, Zinn Macpeak & Seas, PLLC

[57] ABSTRACT

An automatic needle retraction device includes a housing and retraction device for completely retracting a needle back into the housing after use. A selector switch device includes an equalization part, which produces a negative pressure to accept the fluid compressed during the retraction of the hollow needle. Thus, during retraction of the needle, compressed injection solution is not sprayed outward from the needle.

25 Claims, 3 Drawing Sheets

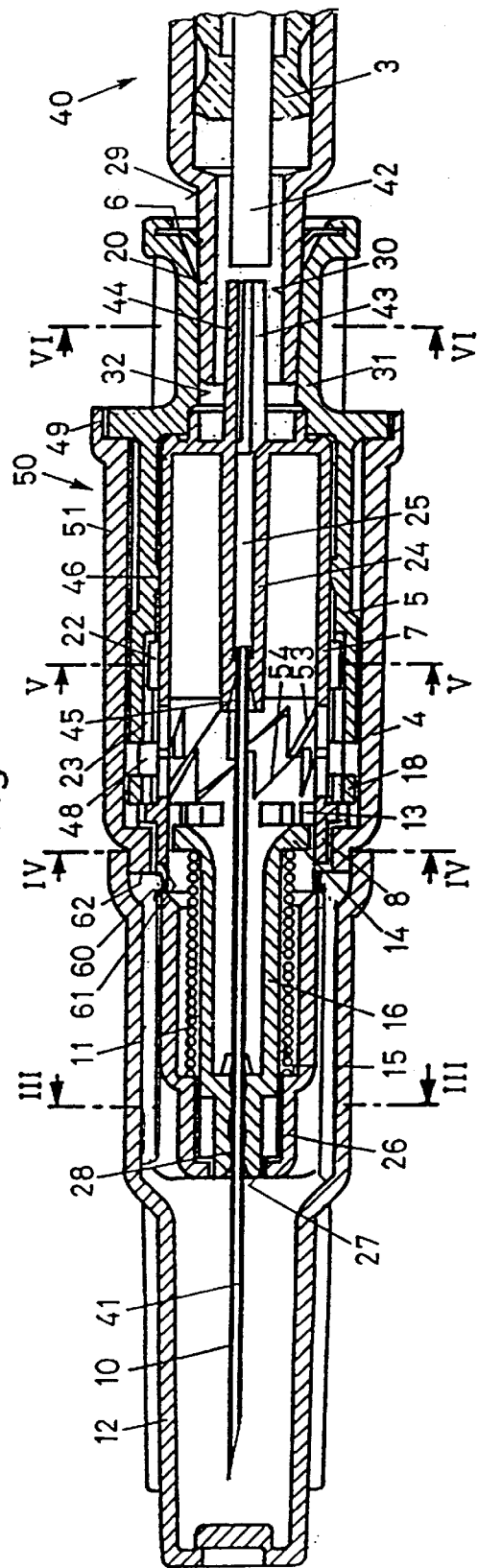
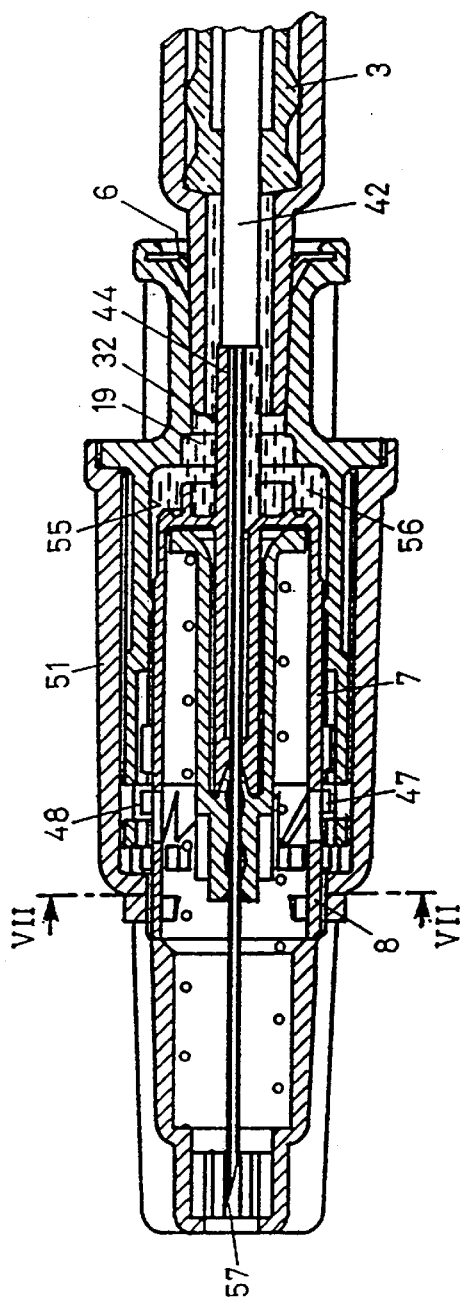

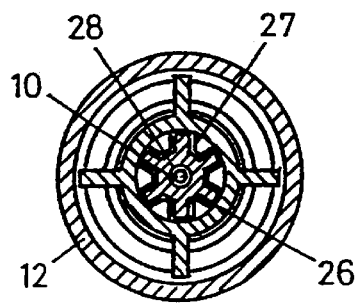
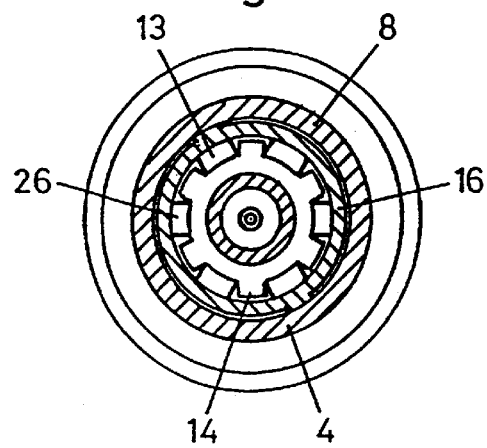
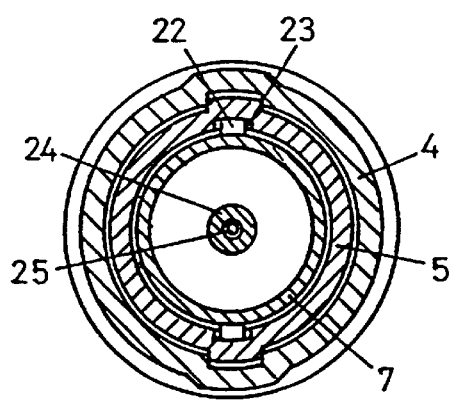
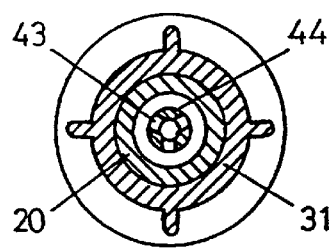
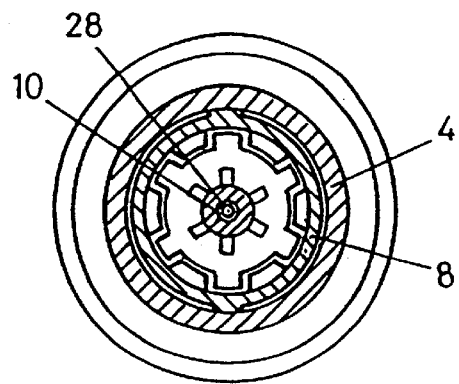

AUTOMATIC CANNULA WITHDRAWING DEVICE FOR INJECTION SYRINGES

The invention concerns a hollow needle consisting of a hollow needle, a device housing and a device by means of which the needle, after being used, can be retracted back into the housing. The complete retraction of the needle into the housing after use will prevent unintentional injury to the user or another person.

In the state of current technology a hollow needle device of this type is known from WO 92/16248. An injection needle is placed prior to use on an hypodermic needle cylinder. Inside the housing the hollow needle is secured by means of a part which during the injection is dissolved or softened. The hollow needle is tensioned for retraction by a pressure spring inside the housing. If the above named part is dissolved or softened by the injection fluid, the fixing of the needle inside the housing is removed and the needle is returned into the housing by the pressure spring. There is the problem with this type of hollow needle that the timing of the initiation of the retraction is not exactly defined. It is also difficult to find a substance that, on the one hand, can be dissolved or softened by the injection fluid and, on the other hand, can unhesitatingly mix with the injection fluid. Probably for these reasons this hollow needle has not met with success in practice.

Another hollow needle device of this type became known in WO 92/05818. In this version the end of the hollow needle is fixed to a holding piece formed on the hypodermic needle cylinder. At the end of the piston stroke this holding piece with a cutting edge attached to a piston is separated from the hypodermic needle cylinder. The base of the hypodermic needle is simultaneously cut through by the cutting edge. Retraction then occurs by means of a pressure spring located in the housing. Tests have shown, that very strong forces are required to cleanly cut through both parts which are made of plastic and rubber. There thus arises a contradiction between the required thin wall of the injection base and the required wall strength to preclude the cold flow of plastic parts under stress to support the spring force. The required wall strength may not exceed a given amount when the long storage time of the hollow needles is taken into consideration.

Although the urgent need for such a hollow needle has been proven, in practice no such needle has as yet proven itself viable.

It is the task of this invention to create a hollow needle of this type which will avoid the above described disadvantages.

SUMMARY OF THE INVENTION

The task is solved for a hollow needle device of the type described by having the device incorporate a selector switch device which can be set to needle retraction after its use. In the hollow needle of this invention the retraction is initiated by the selector switch device. With such a selector switch device the activation timing for retraction can be determined exactly. Separation of plastic parts or a dissolution of substances by the injection fluid is not required with the hollow needle of this invention. The initiation force can be kept very small and the manner of construction can be appropriate for the material involved.

The hollow needle of this invention is envisioned in particular as an injection needle for a hypodermic needle. It can incorporate a Luer's attachment and be made inseparable from the hypodermic needle when placed on it. The hollow needle can, however, be permanently attached to the hypodermic needle from the very outset.

It is essential, that the customary norm requirements be satisfied by the hollow needle of this invention. There thus results a compatibility with standard hollow needles and standard hypodermic needles for emergencies, i.e., when due to circumstances no hypodermic needles or hollow needles of the type of this invention are available. In addition, the selector switch device can be located in a comparably small housing, so that externally the hollow needle can hardly be differentiated from a customary hollow needle. The extractor hollow needles customarily used in hospitals can be replaced by the hollow needles of this invention. As mentioned, a version is, however, conceivable, in which the hollow needle of the invention can be manufactured from the outset as an inseparable part of the hypodermic needle cylinder.

An easily realized construction of the selector switch device is contained in a further development of the invention, when it incorporates a rotatable selector switch part inside the housing on which a retainer permanently attached to the hollow needle is supported. When the selector switch device is activated, the selector switch part is turned to a rotating position in which the retainer with the hollow needle can be retracted into the housing. The retraction movement can occur by means of, for example, a pressure spring. Other energy sources are also conceivable.

In another further development of the invention the selector switch device incorporates an equalizing part with which a negative pressure is created in the injection fluid during the selector switch procedure in order to accept the fluid compressed during the retraction of the hollow needle. The danger can thus be avoided, that during retraction of the hollow needle the injection solution which could be mixed with the blood of the patient is sprayed outward from the hollow needle. The equalizing part thus creates a volume equalization which makes it possible that no compressed fluid is ejected outward during the retraction of the hollow needle.

The invention also concerns an injection hypodermic needle with a hypodermic needle cylinder and a piston rod contained therein with a piston and an exterior cone on which a hollow needle of the invention or a customary hollow needle can be stuck. This injection hypodermic needle is characterized by the means of activating the selector switch device being located on the piston. In such an injection hypodermic needle the selector switch device can be activated by a piston stroke. The means can, for example, incorporate a pin which, after injection, engages into a projection of the hypodermic needle cylinder. The selector switch device would then preferably be activated when the piston seal is pressed down on the hypodermic needle base. This injection hypodermic needle can be operated with one hand, as is customary, and which is a basic advantage in practice. The pin is preferably an extension of the piston rod.

Other advantageous characteristics can be found in the dependent patent claims, the following description and the drawings. An execution model of the invention will be more closely explained from the drawings. They show:

FIG. 1 A longitudinal view of a hollow needle of the invention as well as the attachment of a hypodermic needle.

FIG. 2 A cut in accordance with FIG. 1, but after the retraction of the hollow needle.

FIG. 3 A cross cut through the hollow needle along the line III—III of FIG. 1.

FIG. 4 A cross cut through the hollow needle along the line IV—IV of FIG. 1.

FIG. 5 A cross cut through the hollow needle along the line V—V of FIG. 1.

FIG. 6 A cross cut through the hollow needle along the line VI—VI of FIG. 1.

FIG. 7 A cross cut through the hollow needle along the line VII—VII of FIG. 1.

FIG. 8 A longitudinal cut through an injection hypodermic needle of the invention and an attachment of the hollow needle of the invention.

DETAILED DESCRIPTION OF THE INVENTION

Figure 8:
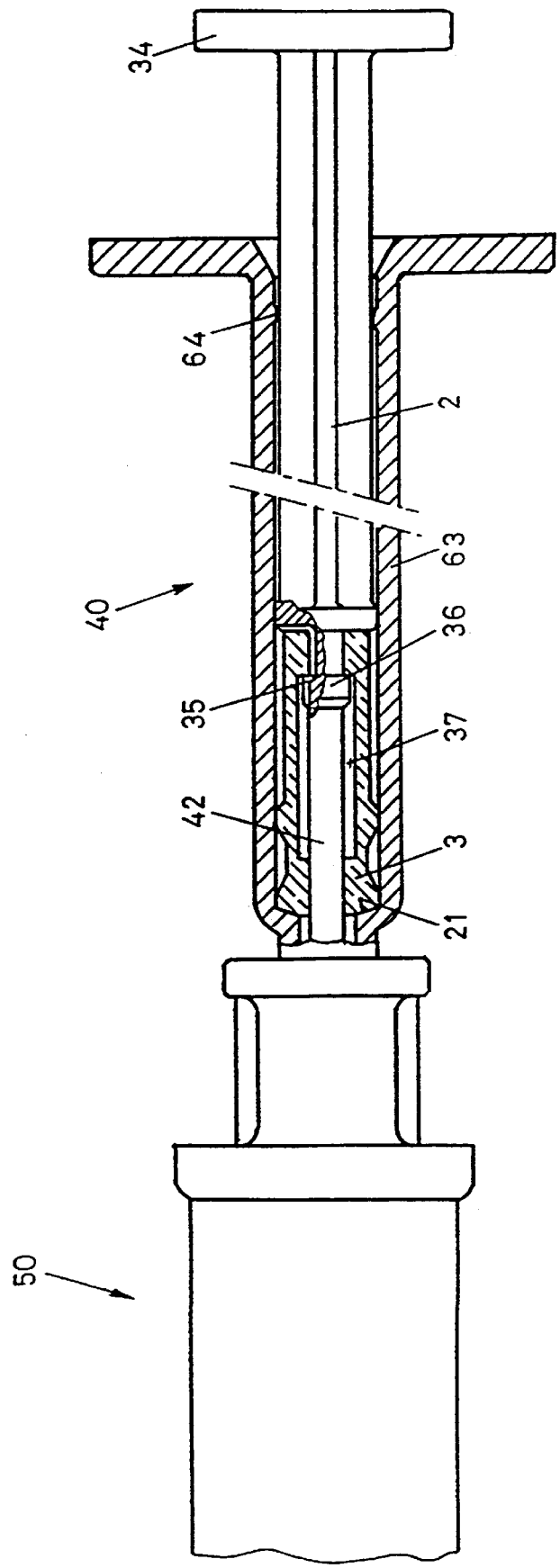

FIG. 1 shows a conical attachment 20 on the housing 23 of an injection hypodermic needle 40 on which a ready made hollow needle device 50 of this invention is placed. The attachment 20 is preferably a Luer's attachment with an outer cone 29. Corresponding to this, a rear part of the housing 5 incorporates an attachment 31 with a corresponding inner cone 32. On the rear end, the attachment 31 has attached a safety ring 6 projecting inward which, when the hollow needle device 50 is attached to the injection hypodermic needle 40, makes the hollow needle 50 inseparable from the attachment 20. A version is conceivable, however, whereby the hollow needle device 50 is separable from the injection hypodermic needle 40.

The rear housing part 5 engages into the front housing part 4 and together form the housing 51. Both housing parts are inseparable joined, for example, by a circular weld joint 49. A removable, protective cap 12 is attached to the forward edge of the front housing part 4. This is removed before using a hollow needle 10 and covers the projecting end of the hollow needle 10. The interior of the protective cap 12 has several cams 60 which each engage into a slit 61 of switch case 8 and prevent it from turning. The front part of the housing 62 is outfitted with longitudinal slits 62 for the cams 60 to engage. The protective cap 12 thus provides a safe means of transportation.

The hollow needle 10 is placed so that it can not move in the center of a clearance hole 28 of a needle holder 16 and is secured against turning. The front end of the needle holder 16 engages into an opening 27 in the front housing part 4 and is secured in this opening 27 against the possibility of turning. The rear end of the needle holder 16 incorporates several radially formed cams 14 projecting outward which rest on inward projecting cams 13 of a switch case 9. A stressed pressure spring 11 which is supported in front on a shoulder 15 of the housing part 4 and on the wide rear end of the needle holder axially stresses the needle holder 16 rearward against the switch case 8. That piece is located in the front housing part 4 and with its rotation limited and is supported on the forward edge 18 of the rear housing part 5. In the area of its edge 18, the rear housing part 5 manifests two opposing recesses 48, each of which engage one of the cams 47 (FIG. 7) of the switch case 8. The cams 47 limit the rotation of the switch case 8 and are located on the rear housing part 5. The switch case 8 is thereby axially fixed, but can rotate radially to a limited degree.

An equalization part 7 which engages the guide grooves 23 of the housing part 5 by means of sideward projecting cams 22 is located in the housing part 5 whereby rotation in relation to the housing 51 is prevented. The guide grooves 23, however, allow the forward displacement of the equalization part 7 against the switch case 8. A circular sealing rib 46 on the interior of the rear housing part 5 seals the equalization part 7 from the housing 51. The sealing effect is maintained during displacement of the equalization part 7 but can also be opened toward the end of the displacement. A tube-shaped guide piece 24 with a continuous channel 25 into which the rear part of the hollow needle 10 engages extends into the interior of the bowl-shaped, equalization part 7. An opening 45, narrowing to the front, in the channel 25 seals the exterior of the hollow needle 10 from the equalization part 7. The opening 45, however, allows a displacement of the hollow needle 10 in the channel 25. The channel 25 terminates at the rear in a broad, tube-shaped projection 44 which manifests along its entire length a continuous, radial slit 43. The channel 25 is thereby open on the side in the area of the projection 45. As clearly seen in FIG. 1, the projection 44 extends into the interior cone 32 and into the clearance hole 30 of the projection 20.

The equalization part 7 can be displaced by means of a pin on the injection hypodermic needle 40 from the position seen in FIG. 1 to the position shown in FIG. 2. As per FIG. 8 the pin 42 is located on the front end of the piston rod 2 and preferably is a continuation of the piston rod 2. The piston rod 2 is outfitted with a customary pressure plate 34. FIG. 8 shows the piston rod 2 in the retracted position following an injection.

The functioning of the hollow needle is described in more detail as follows.

The injection hypodermic needle 40 is filled with injection fluid 19 from an extractor hollow needle not shown here which is mounted on the projection 20. Then the extractor hollow needle is replaced by the injection hollow needle 50 and the protective cap 12 is removed. Finally by means of a short stroke of the retracted piston 3, air can be ejected from the hollow needle 50 to prevent a micro-embolism. The hollow needle 10 can now be inserted into the tissue of a patient. The injection fluid 19 is injected as usual by displacing the piston 3 in the hypodermic needle cylinder 1. The injection solution 19 thereby leaves the hypodermic needle cylinder 1 and the hollow needle 50 by the clearance holes and channels 30, 25 and 41 of the hollow needle 10. Shortly before the end of the injection the pin 42 hits the projection 44 and thereby displaces the equalization part 7 in the longitudinal direction of the hollow needle 50 against the switch case 8. The equalization part 8, which is prevented from turning, hereby turns the switch case 8 by means-of its gear cutting 53 attached on the face and a corresponding gear cutting 54 on the switch case 8. A ring-shaped, intermediate area 56 is simultaneously formed by displacement of the equalization part 7 between it and the interior 55 of the rear housing part 5 and by which a negative pressure is produced in the injection fluid 19. By the turning of the switch case 8 the cams 13 in FIG. 4 are likewise turned and the cams 14 of the needle holder 16 come to rest through gaps 17 between the cams 13. The support of the needle holder 16 on the switch case 8 is thereby removed and the needle holder 16 along with the hollow needle 10 is retracted by the stressed pressure spring 11 into the position shown in FIG. 2. As can be seen, the hollow needle 10 with the forward hypodermic needle 57 is now completely housed in the forward housing part 4. The space 56 created by the displacement of the equalization part 7 accepts the fluid compressed by the retraction of the hollow needle 10 whereby any spraying of fluid through the clearance hole 41 is precluded.

As seen in FIG. 8 the piston 3 is formed like a case and attached at the rear end to the head 36 of the piston rod 2. The piston 3 composed of material made of elastic rubber can be compressed from the position shown in FIG. 8 like an axial bellows in order to initiate another stroke whereby any air present in the passage 37 is ejected to the rear through an air groove 35. The equalization part 7 is displaced by this additional stroke.

In addition a longitudinal equalization which results from varying attachment lengths can be compensated for.

The hollow needle 10 retracted into housing 52 can not be returned either intentionally or unintentionally to the position shown in FIG. 1. On the one hand the hollow needle 10 is hardly accessible from the exterior and on the other hand it must simultaneously be moved forward against the rearward force of the pressure spring 11 and the selector switch part must be turned to the stressed position of the spring. By means of a permanent connection of the hollow needle 50 to the projection 20 of the hypodermic needle 40, for example by means of a securing ring 6, such a retraction of the hollow needle 10 can be further impeded. An inseparable connection also prevents re-use of the hypodermic needle. A rib formed on the interior of the housing 53 forms a block preventing removal of the piston rod 2.

The hollow needle 50 consists of comparably few parts. Plastic parts can be produced out of medically authorized materials, like polypropylene or polyethylene, for injection processes. The needle can be made from normal medicinal steel. A relatively simple assembly of the individual parts is possible and can be automated. Customary norms can be attained with the hollow needle of the invention, but cost-favorable series production is also possible. The use is comparable to customary hypodermic needles which do not retract the hollow needle. One-handed use is possible and no basic forces are required for the retraction of the hollow needle. Initiation of the retraction is timed exactly and can be determined mechanically. It is also essential that the retraction of the hollow needle 10 can be initiated with a high degree of safety after an injection.

We claim:

1. A hollow needle device comprising:

a hollow needle (10);

a housing (51) in which the hollow needle may be housed; and a retraction device for retracting the hollow needle (10), after use, into the housing (51), wherein the retraction device includes a selector switch device (7,8) which can be switched for retraction of the hollow needle (10) after its use, wherein the selector switch device includes an equalization part (7) and by which during a selector switch process a negative pressure is produced to accept a fluid compressed during the retraction of the hollow needle (10).

2. A hollow needle device as per claim 1 wherein the selector switch includes a rotatable selector switch part (8) located in the housing (51) on which a mount (16) permanently connected to the hollow needle (10) is supported.

3. A hollow needle device as per claim 2 wherein the mount (16) permanently holds the hollow needle (10) at a distance from a rear end of the hollow needle (10).

4. A hollow needle device as per claim 2 wherein the mount (16) is stressed by an energy source, especially a pressure spring (11), against the selector switch part (8).

5. A hollow needle device as per claim 2 wherein the mount includes several outward projecting cams (14) on a rear end which are supported on protruding cams (13) of the selector switch part (8).

6. The hollow needle device as per claim 2 the selector switch part (8) is shaped like a case.

7. The hollow needle device as per claim 1 wherein the equalization part (7) possesses a guide part (24) to accept a rear part of a hollow needle (10).

8. The hollow needle device as per claim 1 wherein a rotatable selector switch part (8) is switched by the equalization part (7).

9. The hollow needle device as per claim 8 wherein the equalization part (7) is located in the housing (51) and during a displacement of the equalization part (7), the equalization part engages a selector switch part (8) in order to turn the equalization part.

10. The hollow needle device as per claim 1 wherein the housing (51) includes a front and a rear housing part (4, 5) which are assembled and permanently joined together.

11. The hollow needle device as per claim 10 wherein the rear housing part (5) engages the front housing part (4) and a rotatable selector switch part (8) being supported on the rear housing part (5).

12. The hollow needle device as per claim 10 wherein the equalization part (7) on the rear housing part (5) is positioned so that it axially displaces to the front and rotates.

13. The hollow needle device as per claim 10 wherein the equalization part (7) displaces axially to the front in the housing (51) for switching.

14. The hollow needle device as per claim 10 wherein the housing (51) includes a securing means (6) for inseparably connecting to a hypodermic needle injection device (40).

15. The hollow needle device as per claim 10 wherein the housing (51) includes an inner cone (32) having a rear end into which extends a projection (44) attached to the equalization part (7) in order to activate the equalization part (7).

16. The hollow needle device as per claim 1 wherein a protective cap (12) and a securing means (6) engage the selector switch device (7, 8) to prevent an unintentional retraction of the hollow needle and to allow for safe transportation of the device.

17. The hollow needle device as per claim 16 wherein the protective cap (12) includes protruding cams (60) which engage into recesses (62) on the housing (51).

18. The hollow needle device as per claim 1 wherein a needle holder (16) prevents turning of the hollow needle by engaging the housing (51) of the hollow needle device.

19. The hollow needle device as per claim 1 wherein the hollow needle device includes means (22, 23, 47, 48) to position a front and rear housing and the equalization part (4, 5, 7) during assembly.

20. The hollow needle device as per claim 1 further comprising an injection hypodermic needle with a hypodermic needle cylinder (40) and a piston rod (2) stored therein with a piston (3) on the front end and an exterior cone (29) on which a hollow needle (50) is adaptable to be attached by the means to activate the selector switch device of the hollow needle (50) being attached.

21. The hollow needle device as per claim 20 wherein the hypodermic needle cylinder (40) incorporates a pin (42) to activate the selector switch device which is attached to the piston rod and which after injection engages a projection (20) of the hypodermic needle cylinder (40).

22. The hollow needle device as per claim 20 wherein the piston (3) includes an axially compressible casing whose front end can be placed on a hypodermic needle cylinder base (21).

23. The hollow needle device as per claim 22 wherein the piston rod (2) accepts the rear end of the pin (42).

24. The hollow needle device as per claim 20 wherein the piston (3) is arranged so that a longitudinal equalization due to varying attachment lengths can be compensated.

25. A hollow needle device comprising:

a hollow needle (10);

a housing (51) in which the hollow needle may be housed; and a retraction device for retracting the hollow needle (10), after use, into the housing (51), wherein the retraction device includes a selector switch device (7, 8) which can be switched for retraction of the hollow needle (10) after its use, and wherein the housing (51) includes an inner cone (32) having a rear end into which extends a projection (44) attached to the equalization part (7) in order to activate the equalization part (7).

* * * * *